United States Patent
Suh et al.

[11] Patent Number: 5,859,370
[45] Date of Patent: Jan. 12, 1999

[54] METHOD FOR DETECTING AND SIZING OF CRACKS IN BOLT THREADS BY RAYLEIGH WAVE

[75] Inventors: Dong-man Suh, 119-1401, Hanbit Apt., Oun-Dong, Yusung-Gu; Whan-woo Kim, both of Daejun; Jin-gyun Chung, Chonbuk, all of Rep. of Korea

[73] Assignees: Dong-man Suh; Keun-Sang Lim, both of Rep. of Korea

[21] Appl. No.: 883,733

[22] Filed: Jun. 27, 1997

[30] Foreign Application Priority Data

Dec. 20, 1996 [KR] Rep. of Korea .................. 1996 68457

[51] Int. Cl.$^6$ .................................................. G01N 29/10
[52] U.S. Cl. ................................................. 73/627; 73/622
[58] Field of Search ...................... 364/507, 508; 73/597, 598, 602, 620, 622, 627, 628, 629, 631

[56] References Cited

U.S. PATENT DOCUMENTS

| | | | |
|---|---|---|---|
| 4,052,889 | 10/1977 | Mucciardi et al. | 73/602 |
| 4,274,288 | 6/1981 | Jittman et al. | 73/602 |
| 4,292,848 | 10/1981 | Rainey et al. | 73/602 |
| 4,308,751 | 1/1982 | Thurner et al. | 73/627 |
| 4,479,387 | 10/1984 | Wagner et al. | 73/622 |
| 5,029,480 | 7/1991 | Leibblewhite | 73/761 |
| 5,383,365 | 1/1995 | Battram | 73/598 |
| 5,675,087 | 10/1997 | MacLauchlan et al. | 73/761 |

OTHER PUBLICATIONS

G.M. Light, N.R. Joshi, S.N. Liu "Ultrasonic Detection of Stress–Corrosion Crakcs in Reactor Pressure Vessel and Primary Coolant System Anchor Studs (Bolts)" Materials Evaluation, vol. 45, Dec. 1987 pp. 1413–1418.

NUREG–0933, "Bolting Degradation Of Failure In Nuclear Powerplants" U.S. Nuclear Regulatory Commission, Dec. 31, 1991.

IE Bulletin No. 82–02, "Degradation of Threaded Fasteners in the Reactor Coolant Pressure Boundary of PWR Plants," U.S. Nuclear Regulatory Commission, Jun. 2, 1982.

D. Kishoni, "Application of Digital Pulse Shaping by Least Squares Method to Ultrasonic Signals in Composites," Nasa Bulletin, pp. 781–787.

D. Kishoni, "Removal Dominant Reverberations From Ultrasonic Time–Records Of Layered Material by Digital Predictive Deconvolution" 1987 Ultrasonics Symposium, pp. 1075–1078.

Primary Examiner—Hezron E. Williams
Assistant Examiner—Rose M. Miller
Attorney, Agent, or Firm—Lieberman & Nowak, LLP

[57] ABSTRACT

The present invention is a method of detecting and sizing of a small crack in a root between two crests in stud bolt threads. The key idea is from the fact that the Rayleigh wave is detected between large regularly spaced pulses from the thread. The delay time is the same as the propagation delay time of the slow Rayleigh wave and is proportional to the size of the crack. To efficiently detect the slow Rayleigh wave, three methods based on digital signal processing are proposed; modified wave shaping, dynamic predictive deconvolution, and dynamic predictive deconvolution, and dynamic predictive deconvolution combined with wave shaping.

12 Claims, 11 Drawing Sheets

| NOTCH #1 | L (mm) | D (mm) | W (mm) |
|---|---|---|---|
| 1 | 3.0 | 0.5 | 0.2 |
| 2 | 3.0 | 1.0 | 0.2 |
| 3 | 3.0 | 2.0 | 0.2 |
| 4 | 3.0 | 3.0 | 0.2 |

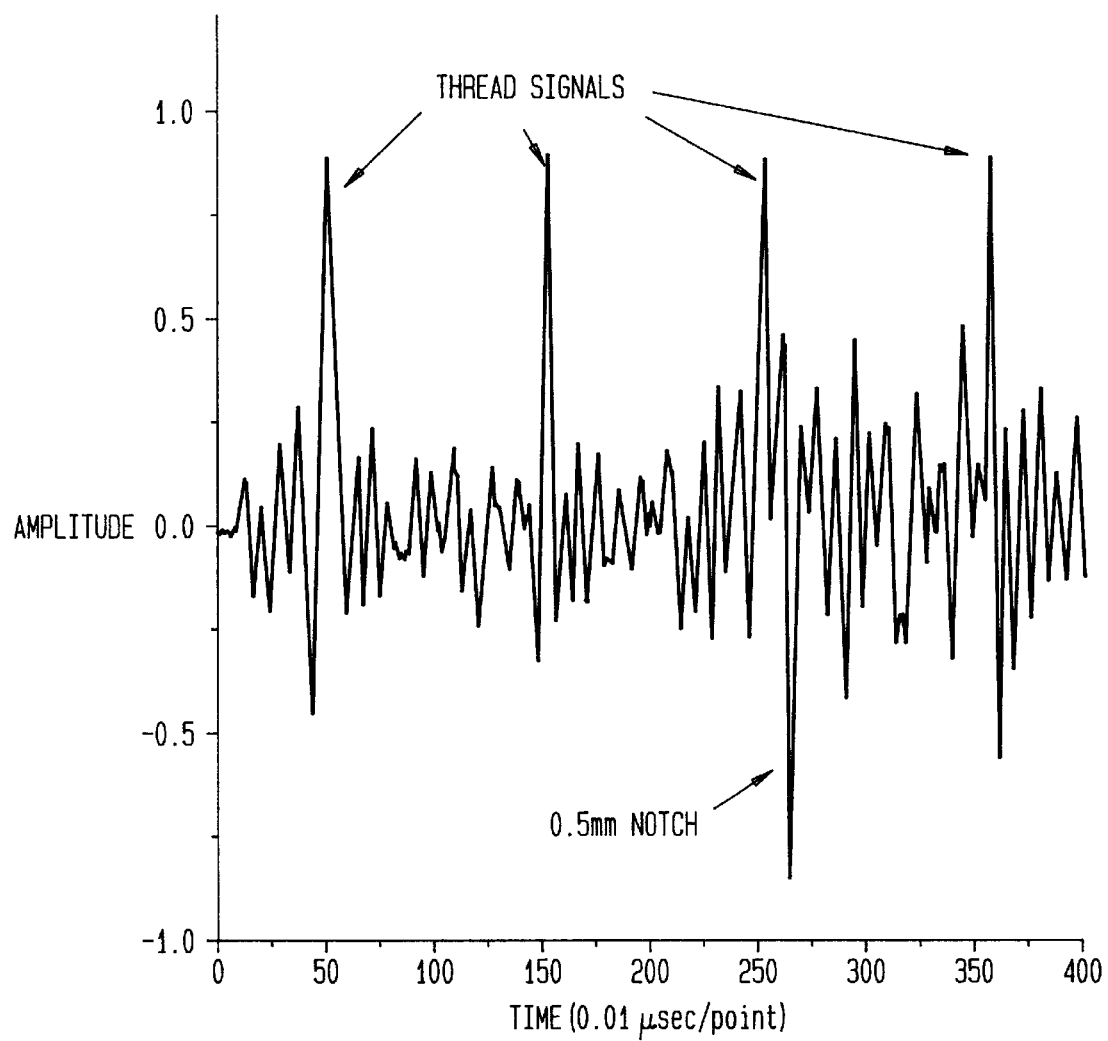

METHOD FOR DETECTING AND SIZING OF CRACKS IN BOLT THREADS BY RAYLEIGH WAVE

BACKGROUND OF THE INVENTION

In the industrial facilities such as nuclear power plants, many kinds and sizes of bolts are used. But bolt degradation has become a major issue in the nuclear industry since the 1980's due to failure during operation. If small cracks in stud bolts are not detected early enough, they grow rapidly and cause catastrophic disasters. Their detection, despite its importance, is known to be a very difficult problem due to the complicated structures of the stud bolts.

Generally, ultrasonic, magnetic particle and eddy current testing procedures are carried out for bolt inspection. Among these, ultrasonic inspection is the only one which is expected to detect cracks in the thread region, under the condition that the studs and bolts are not removed. However, by conventional ultrasonic testing methods, it is difficult to detect flaws such as stress-corrosion cracks or corrosion wastage in the threads. In many cases, a small flaws signal can hardly be distinguished from the complicated signals reflected from threads. When the flaw is quite small, the signal amplitude reflected from it is nearly equal in size to the noise level.

Therefore, there exits a need for a method for detection of cracks in a stud bolt that distinguishes the small signal from the flaws in the stud bolt from the complicated signals reflected from threads of the stud bolt.

SUMMARY OF THE INVENTION

The need is met through provision of the method for detecting cracks in a stud bolt disclosed as below. The present invention provides a method for detecting and sizing of small cracks in a root between two crest in threads, the method comprising radiating an ultrasonic wave into the flank of the bolt threads with an incident angle other than 90 degrees; detecting a reflected signal which is one of regularly spaced signals which are reflected from the threads; detecting a Rayleigh wave signal, which is from the Rayleigh wave propagating along the crack from the tip to the opening and reflected from the opening mouth; measuring the elapsed time beginning from the reflected signal and ending at the Rayleigh wave signal; and calculating the crack size by the elapsed time.

The present invention also provides a method for detecting and sizing of small cracks in a root between two crest in threads, the method comprising: radiating an ultrasonic wave into the flank of the bolt threads with the incident angle being other than 90 degrees; detecting a tip diffracted signal which is reflected from the crack tip; detecting a reflected signal which is one of the regularly spaced signals which are reflected from the threads; measuring the elapsed time beginning from the tip diffracted signal and ending at the reflected signal; and calculating the crack size by the elapsed time.

BRIEF DESCRIPTION OF THE DRAWINGS

FIG. 4A for 0.5 mm notch, FIG. 4B for 1.0 mm notch, FIG. 4C for 2.0 mm notch, FIG. 4D for 3.0 mm notch.

FIG. 5A for 2.0 mm notch, FIG. 5B for 3.0 mm notch.

FIG. 8 shows a processed signal by the provided wave shaping method according to the invention.

DETAILED DESCRIPTION OF THE INVENTION

Figure 1:
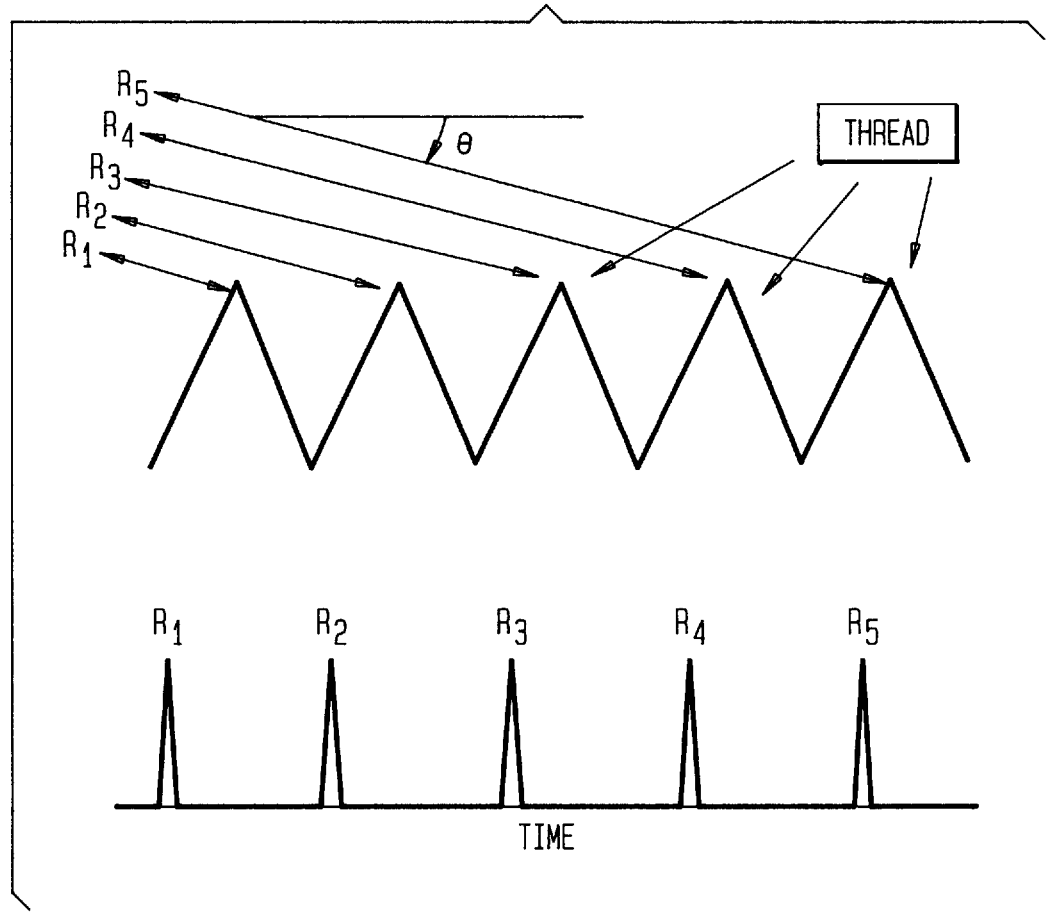
FIG. 1 is a schematic diagram showing ray path for reflections from roots of thread.

When ultrasonic beam travels into a thread region, there is almost same interval(delay time) between echoes from any two successive threads as schematically shown in FIG. 1. If the incident beam is perpendicular to the flank of a thread, the pulse-echo signal will be dominated by a strong back scattered reflection from the flank, with the weaker diffracted waves from the thread root arriving at the same time. If the incident beam angle to the flank of a thread if other than 90 degree, the reflected ultrasonic energy from the flank of the thread will not be strongly detected in a pulse-echo measurement, with the diffracted root signal being the major response. Actually, the thread signals become smaller and less well recognizable while propagating through the bolt due to ultrasonic attenuation and noise in the medium. But we can detect and size a small crack in a thread from the small signals between the thread signals as follows.

If bolt threads are in a good condition without any crack, the delay times between the travel time of the signals from two successive threads are the same. But if there is any small crack in the thread which starts at the base of the thread root and proceeds at right angles to the bolt axis, the delay times of signals from the root of a thread are different from those of normal thread signal.

Figure 2:
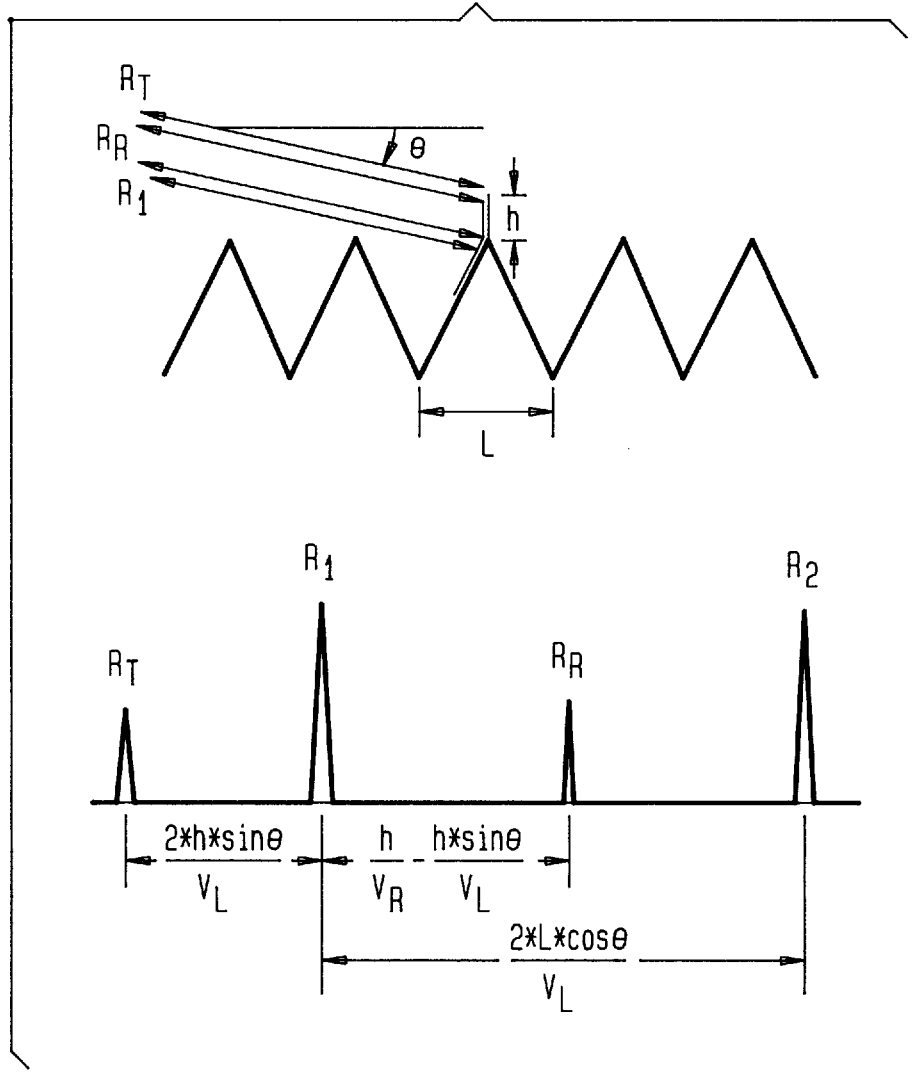
FIG. 2 is a schematic diagram showing ray path for reflections from a crack at the root of a thread.

FIG. 2 shows further detail on this situation for the case of longitudinal-wave, angle-beam illumination. When an angled ultrasonic beam encounters a crack in the root of a thread, some of the energy is converted into various waves diffracted or reflected from the tip of the crack and the intersection of the thread root and crack, as shown in FIG. 2. The relevant echoes are: $R_T$, which is diffracted by the crack tip, $R_1$, which is diffracted from the intersection of the crack and root of the thread, and $R_R$, which travels as Rayleigh wave along the crack face and radiates from the mouth where the crack opens at the root of the thread. $R_2$ is signal which is diffracted from the root of the next thread. The signal, $R_1$, from the thread is enhanced by the presence of the crack, but the metal path and hence arrival time is almost unchanged from the crack free case. The tip signal, $R_T$, precedes $R_1$ and Rayleigh wave, $R_R$ occurs after the main echoes $R_1$. Thus, we can estimate the crack size by the delay times of either of these signals.

Consider the Rayleigh wave delay time $\Delta t_R$ of signal $R_R$. By simple reasoning, it can be seen that the delay time by which $R_R$ follows $R_1$ is given by below equation (1).

$$\Delta t_R = h/V_R - h\sin\theta/V_L \tag{1}$$

where, $\Delta t_R$ is a delay time between thread root and Rayleigh wave signal, $V_R$ is the Rayleigh wave speed (2800 m/sec in steel), $V_L$ is the longitudinal wave speed (5800 m/sec in steel), $\theta$ is an angle between incident wave and bolt axis and h is a crack size.

Therefore, we can estimate the crack size by below equation (2).

$$h = \Delta t_R V_R V_L / (V_L - V_R \sin\theta) \tag{2}$$

Also, we can estimate the crack size by the delay time $\Delta t_T$ between the tip diffracted signal, $R_T$, and the main signal $R_1$. It can be easily seen that the delay time between these echoes is given by below equation (3), $$\Delta t_T = 2h\sin\theta/V_L \tag{3}$$

so that the crack height can be estimated by below equation (4), $$h = \Delta t_T V_L / (2\sin\theta) \tag{4}$$

where, $\Delta t_T$ is the delay time between the tip-diffracted signal and the thread root signal.

On the other hand, when using the shear-wave, angle-beam technique to detect a small crack in the thread, one should substitute the shear speed, $V_T$, in place of the longitudinal wave speed, $V_L$, in equation (1)–(4).

Figure 3:
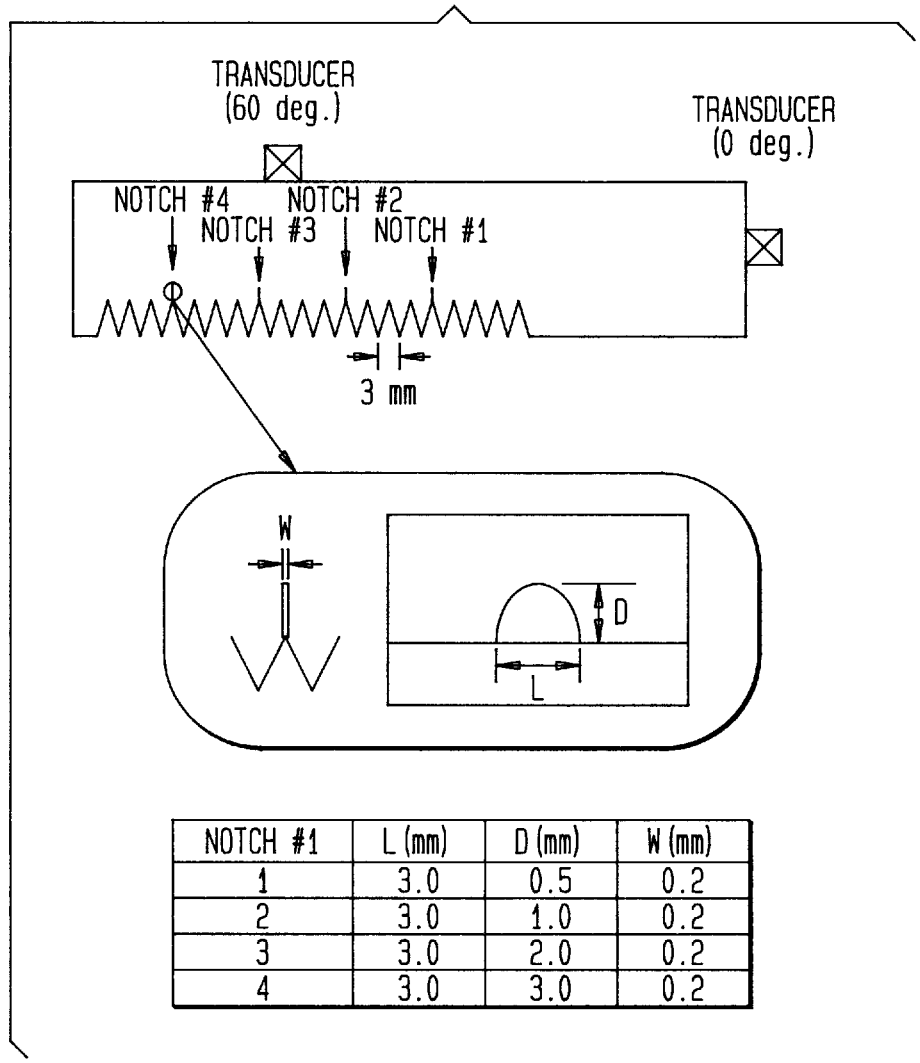
FIG. 3 shows a dimension of the test specimen.

To test the theory, a carbon steel test specimen was fabricated with threads, and notches were machined into the test specimen location as shown in FIG. 3. The pitch to pitch interval is 3 mm. The notches are produced by EDM techniques with 0.5, 1.0, 2.0 and 3.0 mm depth, 0.2 mm width, and 0.3 mm length.

We have to select the center frequency of transducer in order to discriminate successive thread echoes. The center frequency of the transducer must be greater than twice the pulse train frequency of the thread signals. When pitch to pitch interval is 3 mm and the angle between incident wave and thread wall is nearly zero in the longitudinal-wave, straight-beam case, the pulse train frequency from threads is approximately 1 MHz in pulse-echo technique. In the 60 degree shear-wave, angle-beam technique, the pulse train frequency from threads is approximately 0.5 MHz. The center frequency of transducers used in the test, 10 MHz, thus satisfies the above criteria and also gives good resolution.

FIG. 4 shows the amplitude-scan display of the signals from stud threads containing the notches as observed in the longitudinal-wave, straight-beam technique. Threads with notches 0.5 mm deep produced very low amplitude signals, while those with 1.0, 2.0, 3.0 mm notches produced higher amplitude signals than the notch free thread noise. A expanded A-scan display showing the 0.5 mm notch signal is shown in FIG. 4A. The notch signal $R_1$ is reflected from the corner of the crack and thread root. As there is a small crack at the thread root, the signal $R_R$, which travels as a Rayleigh wave along the crack face and radiates from the crack mouth occurs after the thread signal $R_1$. But since the tip diffracted signal ($R_T$) almost overlaps with $R_1$ signal in time and is very weak in amplitude, it is not resolved.

Figure 4A:
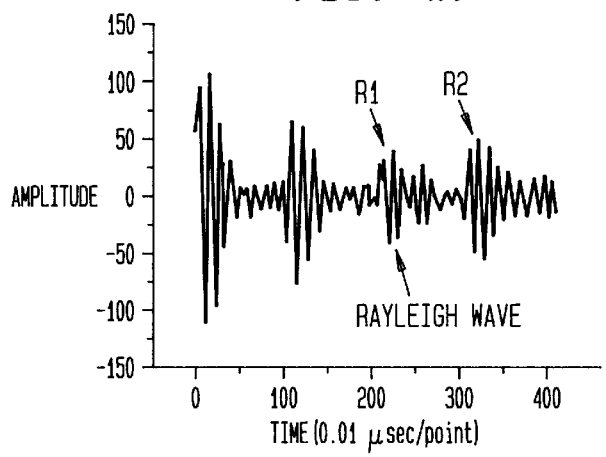
FIG. 4A–D are ultrasonic signals from threads with notches using the longitudinal-wave, straight-beam technique.
Figure 4B:
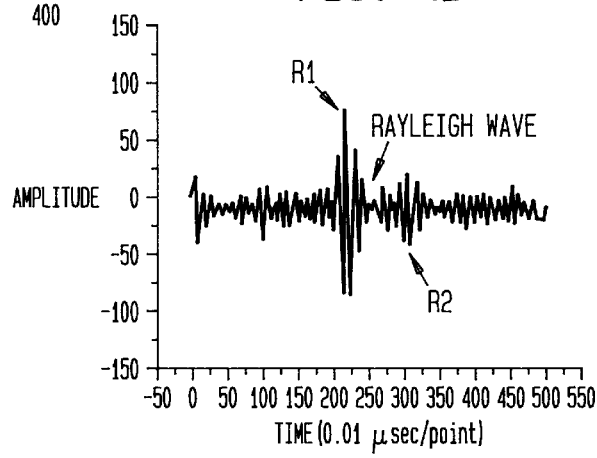
Figure 4C:
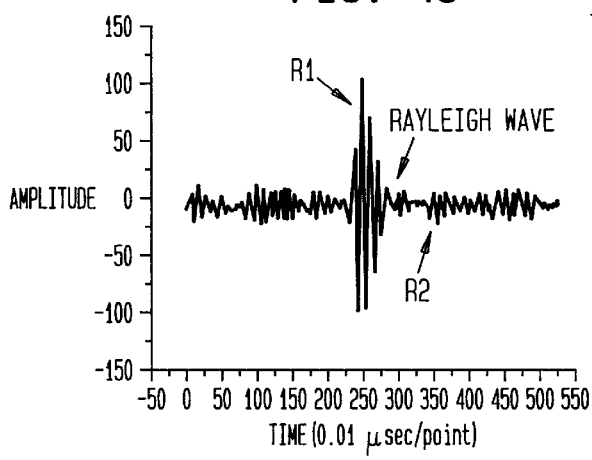
Figure 4D:
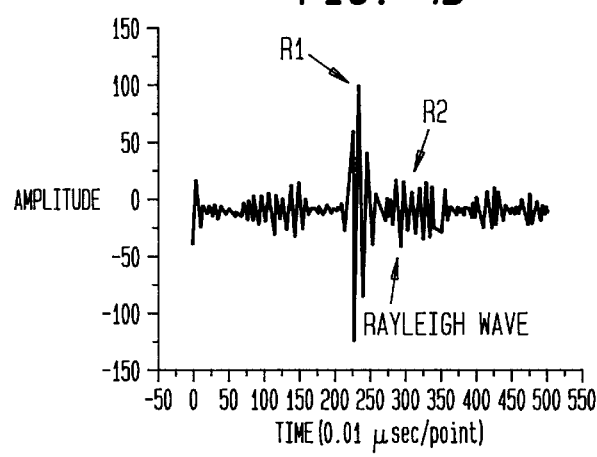

For the 1-mm notch, as shown in FIG. 4B, the signal $R_R$ is again seen. In addition, the signal $R_1$ is considerably larger than $R_2$. These trends continue in FIG. 4C and FIG. 4D. In particular, the amplitude of the trailing thread signal ($R_2$) is decreased because the sound path is interrupted by the notch. As the crack size increases, the echo amplitude of signal ($R_2$) decreases and eventually disappears due to acoustic shadowing. But the Rayleigh wave appears after the notch signal (R1) in FIG. 4B, FIG. 4C and FIG. 4D, therefore the crack size can be determined by above equation (2).

Figure 5A:
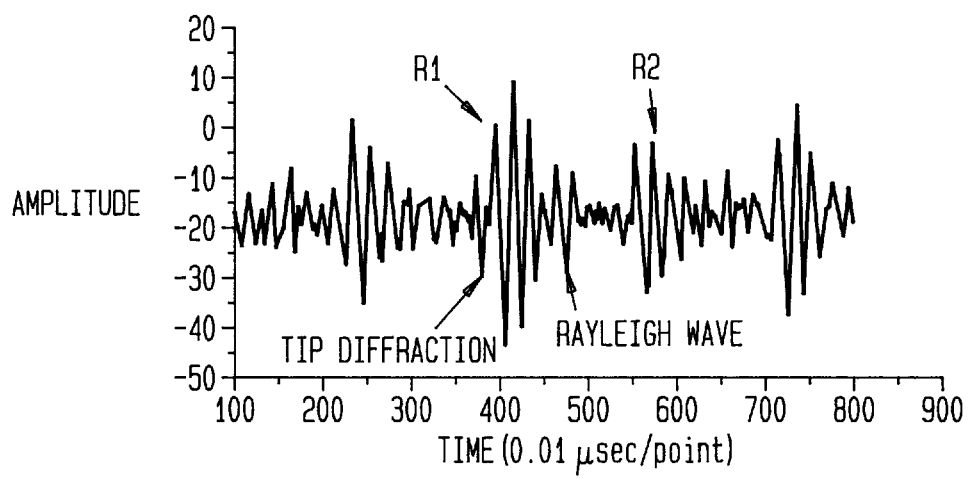
FIG. 5A–B are ultrasonic signals from threads with notched using the shear-wave, angle-beam technique.
Figure 5B:
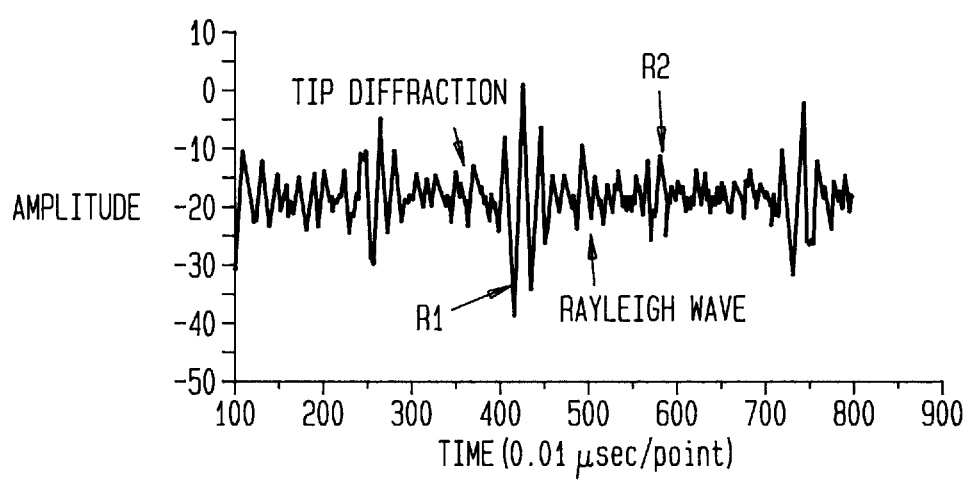

For the shear-wave, angle-beam examination, a 60-degree transducer was used. FIG. 5A and FIG. 5B show the thread signal with 2.0 and 3.0 mm deep notches. The notched thread signal ($R_1$) is reflected at the corner of the notch and thread root. In FIG. 5A and FIG. 5B, the Rayleigh wave, $R_R$, appears after the notch signal, $R_1$. However, it was difficult to discriminate Rayleigh wave signal $R_R$ after $R_1$ for 0.5 mm and 1.0 mm notches.

To determine the location and the size of a small crack in the stud and bolt threads, it is important to enhance the sharpness of the ultrasonic waveforms. In the present invention, a wave shaping method is provided to improve the resolution of the system. Firstly, we describe a conventional wave shaping technique in order to understand the improved method according to present invention.

Given a reference signal a(n), we want to find the mathematical operator f(n) that will transfer a(n) into a desired waveform d(n) by the convolution of a(n) with f(n) as following equation (5)

$$d(n) = a(n) * f(n) \tag{5}$$

where, (*) means the convolution operation. However, the finite length of f(n) will introduce errors and consequently the waveform q(n) computed by the convolution of a(n) with finite length f(n) is not equal to the desired waveform d(n). When the length of f(n) is m+1, q(n) is computed as following equation (6).

$$q(n) = \sum_{s=0}^{m} f(s)a(n-s), \quad n = 0,1,\ldots,m+N \tag{6}$$

$$= 0, \quad n > m+N$$

where, N+1 is the length of the reference waveform. Thus it is necessary to obtain the optimized coefficients of finite length f(n) that will result in a reduced error. In the present invention, the error is defined in the least-squares sense as following equation (7).

$$E = \sum_{n=0}^{\infty} (d(n) - q(n))^2 \tag{7}$$

From the above equations (6) and (7), error E can be expressed as following equation (8).

$$E = \sum_{n=0}^{m+N} \left( d(n) - \sum_{s=0}^{m} f(s)a(n-s) \right)^2 + \sum_{n=m+N+1}^{\infty} d(n)^2 \tag{8}$$

The optimized coefficients of f(n) can be found by minimizing the error E in the above equation (8). By the following equation (9) we obtain the following equation (10).

$$\frac{\partial E}{\partial f(n)} = 0, n = 0,1,\ldots,m \tag{9}$$

-continued
$$\sum_{s=0}^{m} f(s) \sum_{n=0}^{m+N} a(n-s)a(n-j) = \sum_{n=0}^{m+N} d(n)a(n-j), \quad (10)$$

$$j = 0, 1, \ldots, m$$

By defining $r_{j-s}$ and $g_j$ as following equation (11), the above equation (10) can be expressed as the following equation (12).

$$r_{j-s} = \sum_{n=0}^{m+N} a(n-s)a(n-j), \quad (11)$$

$$g_j = \sum_{n=0}^{m+N} d(n)a(n-j)$$

$$\sum_{s=0}^{m} f(s)r_{j-s} = g_j, j = 0, 1, \ldots m \quad (12)$$

Notice that $r_{j-s}$ is the autocorrelation of $a(n)$ and $g_j$ is the correlation of $d(n)$ with $a(n)$. Thus, the optimized coefficients of $f(n)$ can be obtained by solving the following matrix equation (13).

$$\begin{bmatrix} r_0 & r_1 & \cdots & r_m \\ r_1 & r_0 & \cdots & r_{m-1} \\ \cdot & \cdot & & \cdot \\ \cdot & \cdot & & \cdot \\ \cdot & \cdot & & \cdot \\ r_m & r_{m-1} & \cdots & r_0 \end{bmatrix} \begin{bmatrix} f(0) \\ f(1) \\ \cdot \\ \cdot \\ \cdot \\ f(m) \end{bmatrix} = \begin{bmatrix} g_0 \\ g_1 \\ \cdot \\ \cdot \\ \cdot \\ g_m \end{bmatrix} \quad (13)$$

The minimized error will be then as following equation (14).

$$E_{min} = \sum_{n=0}^{\infty} d(n)^2 - \sum_{n=0}^{m} f(n)g(n) \quad (14)$$

Even if the operator is computed by the above equation (13) using a reference signal from a root of threads without any crack, the performance of the operator is not satisfactory in some cases due to the minute differences between the signals from threads. The performance can be improved significantly by the following modified least squared method.

If we use two reference signals $a_1(n)$ and $a_2(n)$ from threads without any cracks, the error E in equation (8) can be rewritten as the following equation (15).

$$E = \sum_{n=0}^{m+N} \left( 2d(n) - \sum_{s=0}^{m} f(s)a_1(n-s) - \sum_{s=0}^{m} f(s)a_2(n-s) \right)^2 + \sum_{n=m+N+1}^{\infty} d(n)^2 \quad (15)$$

To obtain optimized operator coefficients, the above equation (9) is applied to the equation (15), which gives the following equation (16).

$$2 \left( \sum_{n=0}^{m+N} d(n)a_1(n-j) + \sum_{s=0}^{m+N} d(n)a_2(n-j) \right) = \quad (16)$$

$$\sum_{s=0}^{m} f(s) \left[ \sum_{n=0}^{m+N} a_1(n-s)a_1(n-j) + \sum_{n=0}^{m+N} a_2(n-s)a_1(n-j) + \sum_{n=0}^{m+N} a_1(n-s)a_2(n-j) + \sum_{n=0}^{m+N} a_2(n-s)a_2(n-j) \right]$$

-continued
$$j = 0, 1, \ldots, m.$$

Using the above equation (11), the above equation (16) can be represented as the following equation (17).

$$\sum_{s=0}^{m} f(s)[r_{11(j-s)} + r_{21(j-s)} + r_{12(j-s)} + r_{22(j-s)}] = 2[g_{1(j)} + g_{2(j)}], \quad (17)$$

$$j = 0, 1, \ldots, m$$

where $r_{k1}$ if the correlation of $a_k(n)$ with $a_1(n)$ and $g_k$ is the correlation of $d(n)$ with $a_k(n)$.

The optimized operator can be obtained from the above equation (170 and the minimized error will be as the following equation (18).

$$E_{min} = 4 \sum_{n=0}^{\infty} d(n)^2 - 3 \sum_{s=0}^{m} f(s)[g_{1(s)} + g_{2(s)}] + \quad (18)$$

$$4 \sum_{n=0}^{m+N} \left[ \sum_{s=0}^{m} f(s)a_1(n-s) \sum_{s=0}^{m} f(s)a_2(n-s) \right]$$

In general, when the number of reference waveform is $\alpha$, the optimized operator can be obtained from the following equation (19).

$$\sum_{s=0}^{m} f(s) \sum_{l=1}^{\alpha} \sum_{k=1}^{\alpha} r_{lk(j-s)} = \alpha \sum_{l=1}^{\alpha} g_{l(j)}, j = 0, 1, \ldots, m \quad (19)$$

Figure 6:
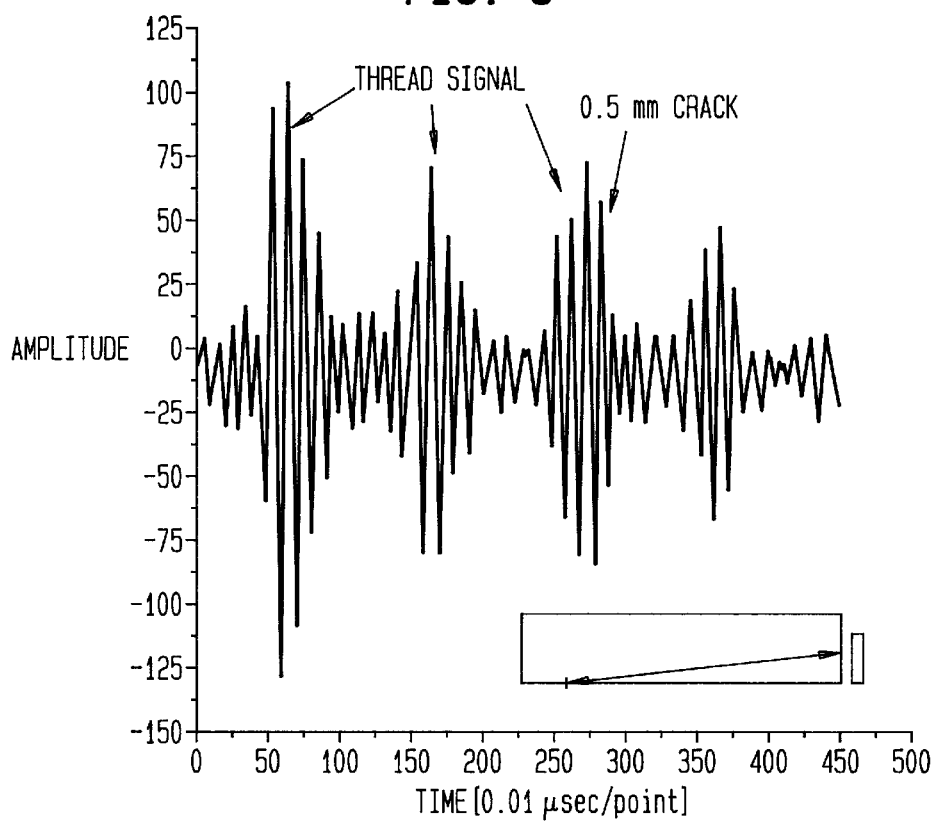
FIG. 6 is a ultrasonic signal from threads with a 0.5 mm crack.
Figure 7:
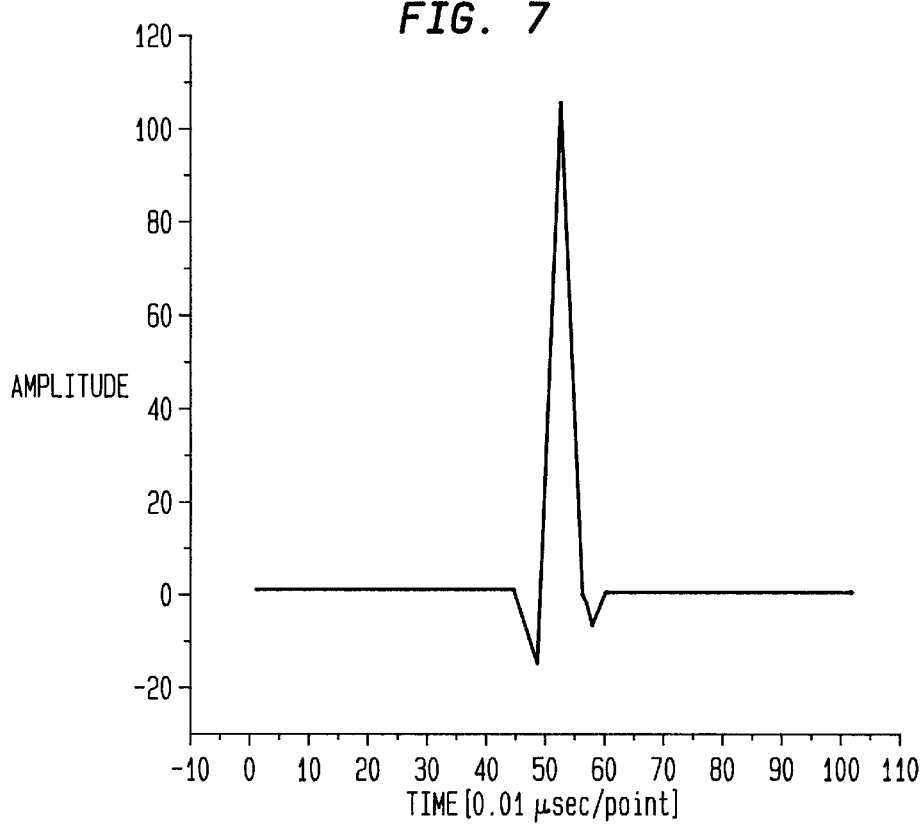
FIG. 7 is a desired signal for wave shaping method.

FIG. 6 shows a ultrasonic signal obtained from threads with a crack. The center frequency of the transducer is 10 MHZ. In this case, as can be seen from the FIG. 6, it is difficult to detect a Rayleigh wave. To apply our wave shaping method to this case, the desired signal in FIG. 7 is used. Two reference signals were used to find the optimized operator coefficients. Thus, the optimized operator coefficients are obtained from the above equation (19) with $\alpha=2$. By applying the operator to the signal in FIG. 6, the processed signal is obtained as shown in FIG. 8. From FIG. 8, the small crack can be easily detected.

As the ultrasonic waves continue to propagate through a material, the waves experience some exponential type attenuation. To compensate for this, we use the concept of window by which each wave is normalized to unity, as can be seen in FIG. 8.

As can be seen from FIG. 1, ultrasonic signals from studs and bolts have strong reflections from roots of threads. To efficiently determine the location and the size of a small crack, these large regularly spaced pulses can be removed by predictive deconvolution technique. Based on the fact that the large regularly spaced pulses are correlated each other, the predictive deconvolution estimates the next signal value using the previous signal values, over a predictive distance. An optimized operator is used to remove the predicted regular signal so that the events such as defects can be extracted and investigated more easily.

After briefly summarizing the predictive deconvolution technique, we propose dynamic predictive deconvolution method where predictive distance for each prediction is adjusted from the previous predictive distance depending on the test environments.

If it takes $T_1$ seconds for a ultrasonic wave to travel from a thread root to the next thread root, the time interval between two consecutive echoes is $2T_1$. Let the incident wave from the transducer to the threads is x(t). Then the reflected wave R(t) from the threads can be expressed as the following equation (20).

$$R(t) = \sum_{k=1}^{N} R_k x(t - 2kT_1) \quad (20)$$

where, N is the number of threads and $R_x$ is the amplitude of the reflected wave determined by the attenuation characteristics of the threads.

Let the sampled version of R(t) be noted by R(n). If the length of the prediction operator p is m+1 and the number of sample points corresponding to the distance between two consecutive thread roots is D, then the error between the actual signal and the predictive signal (for example, the error between $R_2$ and estimated $R_2$ predicted from $R_1$ in FIG. 1) can be expressed as the following equation (21).

$$E = \sum_{n=0}^{D-1} \left( R(n+D) - \sum_{s=0}^{m} p(s)R(n-s) \right)^2 \quad (21)$$

The optimized prediction operator can be found by the following equation (22).

$$\frac{\partial E}{\partial p(n)} = 0, n = 0,1, \ldots m. \quad (22)$$

From the above equation (22), $$\sum_{s=0}^{m} \sum_{n=0}^{D-1} p(s)R(n-j)R(n-s) = \sum_{n=0}^{D-1} R(n+D)R(n-j) \quad (23)$$

$j = 0,1, \ldots m.$

By defining $r_{j-s}$ as the following equation (24), $$r_{j-s} = \sum_{n=0}^{D-1} R(n-j)R(n-s), \quad (24)$$

the above equation (23) can be expressed as the following equation (25).

$$\sum_{s=0}^{m} p(s)r_{j-s} = r_{j+D}, j = 0,1, \ldots m. \quad (25)$$

Thus the optimized coefficients of p(n) can be obtained by solving the following matrix equation (26).

$$\begin{bmatrix} r_0 & r_1 & \ldots & r_m \\ r_1 & r_0 & \ldots & r_{m-1} \\ . & . & & . \\ . & . & & . \\ . & . & & . \\ r_m & r_{m-1} & \ldots & r_0 \end{bmatrix} \begin{bmatrix} p(0) \\ p(1) \\ . \\ . \\ . \\ p(m) \end{bmatrix} = \begin{bmatrix} r_D \\ r_{D+1} \\ . \\ . \\ . \\ r_{D+m} \end{bmatrix} \quad (26)$$

Figure 9A:
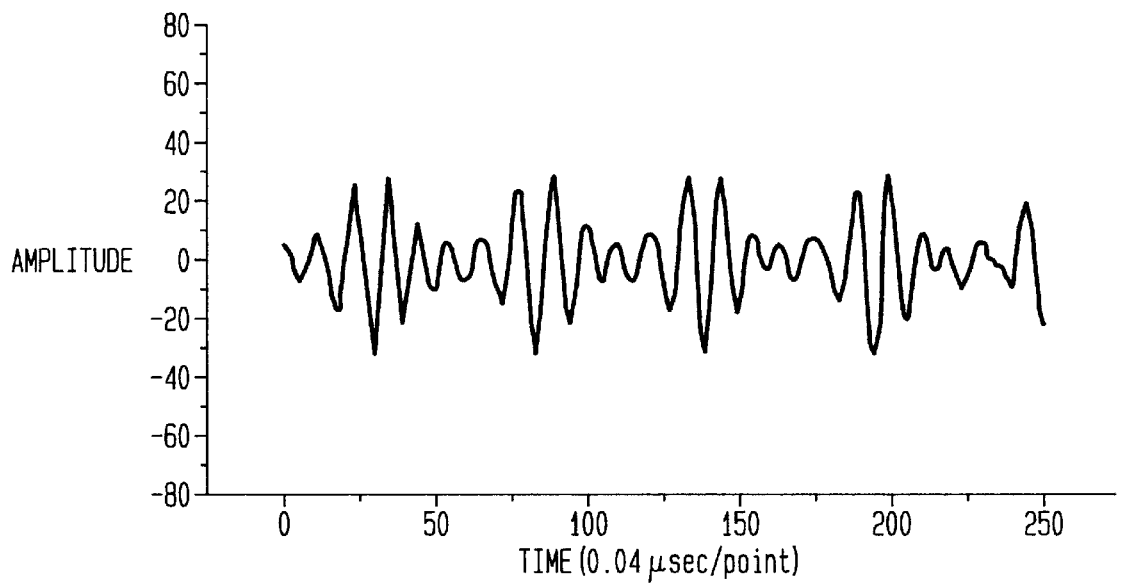
FIG. 9A for signal received at a transducer, FIG. 9B for processed signal by predictive deconvolution.
Figure 9B:
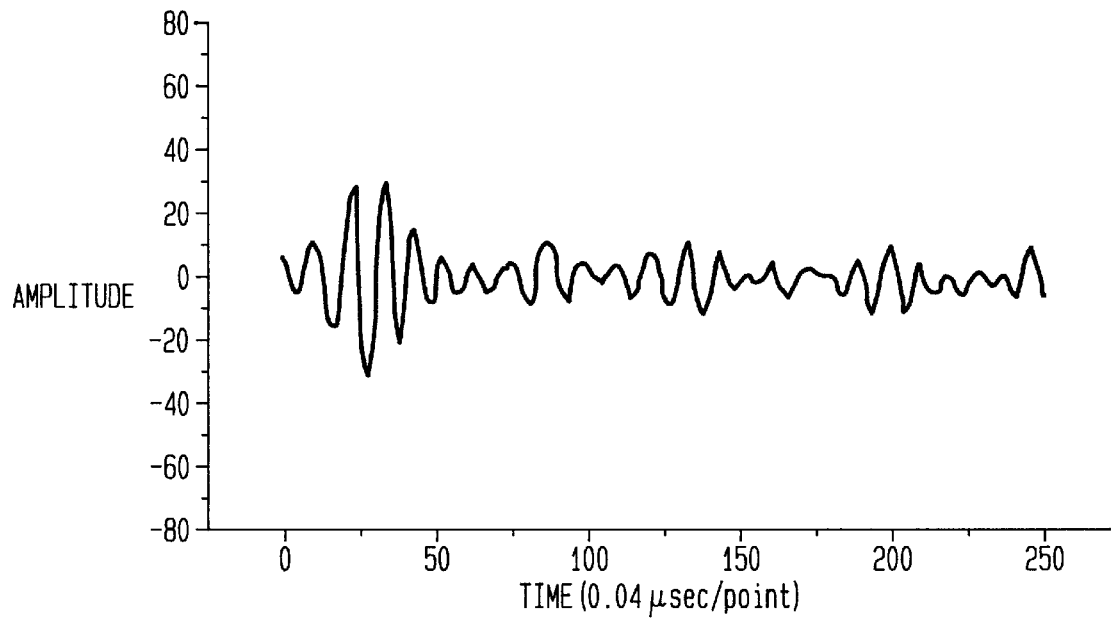
FIG. 9 shows an application of predictive deconvolution technique.

Using the optimized coefficients, the estimated value for R(n+D) can be computed as $\sum_{s=0}^{m} p(s)R(n-s)$. An application example of the predictive deconvolution technique is shown in FIG. 9.

In convolution predictive deconvolution technique, it is assumed that the prediction distance D is constant. Although this assumption is valid for many applications, D needs to be adjusted to $D+\delta_i$ for I-th prediction depending on the location of the transducer, the structure of bolt threads, and the sampling frequency.

Figure 10:
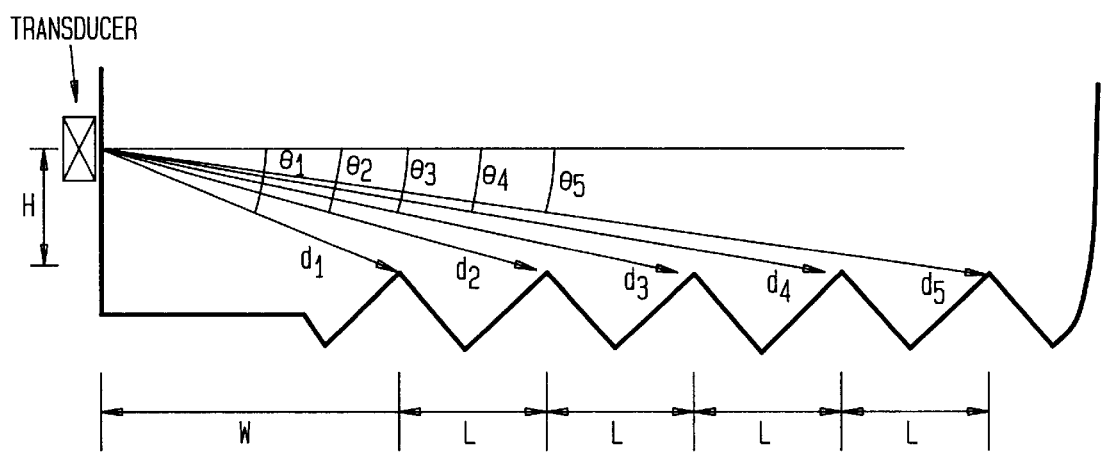
FIG. 10 shows a test environment of the location of the transducer and the structure of thread roots.

Consider FIG. 10 which shows the location of the transducer and the structure of thread roots. The distances from the transducer and the thread roots are: $d_1=W\cos\theta_1$, $d_2=d_1+L\cos\theta_2$, $d_3=d_2+L\cos\theta_3$, $d_4=d_3+L\cos\theta_4$, .... The angles can be computed as $\theta_1=\tan^{-1}(H/W)$, $\theta_2=\tan^{-1}(H/(W+L))$, $\theta_3=\tan^{-1}(H/(W+2L))$, $\theta_4=\tan^{-1}(H/(W+3L))$, .... Thus, $$d_{i+1} - d_i = L\cos\theta_{i+1} = \quad (27)$$

$$L\cos\left(\tan^{-1}\left(\frac{H}{W+iL}\right)\right), i = 0,1,\ldots,N-1.$$

In the proposed dynamic predictive deconvolution method, the prediction distance is adjusted according to the above equation (27) for each prediction.

In predictive deconvolution method, prediction for k-th signal $R_x(t-2kT_1)$ is performed based on (k-1)-th signal $R_{k-1}x(t-2(k-1)T_1)$. However, if (k-1)-th signal contains errors, the prediction for k-th signal cannot be accurate. Thus, in the proposed dynamic predictive deconvolution method, each prediction is performed based on the first received signal $R_1x(t-2T_1)$.

Figure 11A:
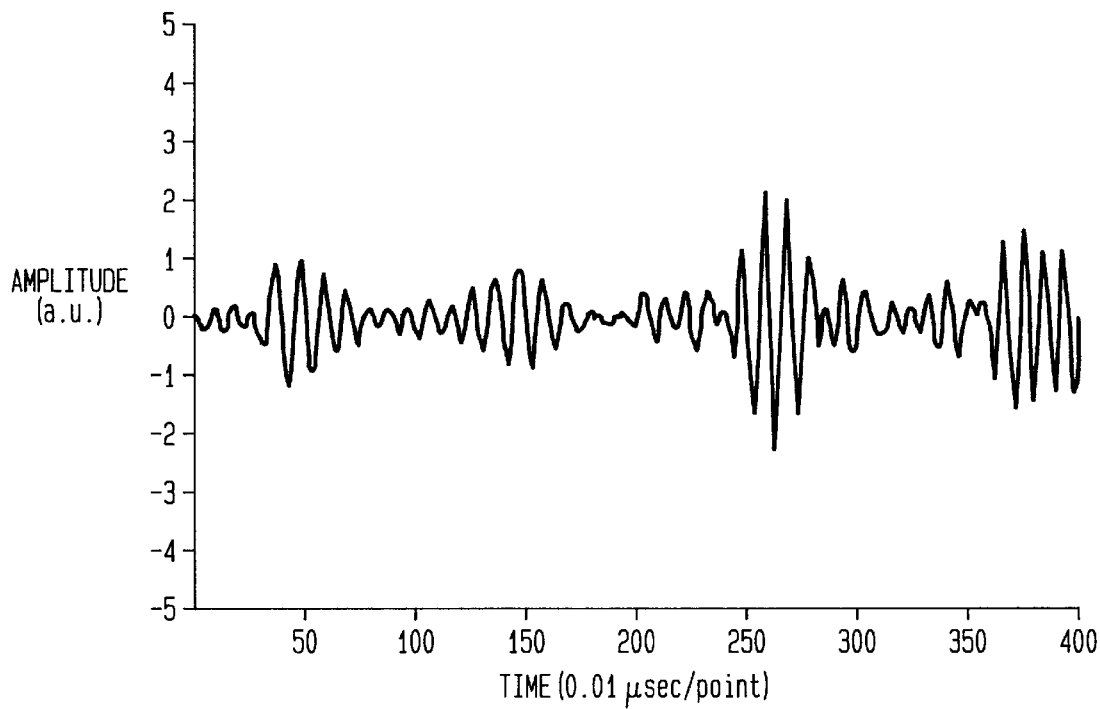
FIG. 11A for signal processed by predictive deconvolution, FIG. 11B for signal processed by dynamic predictive deconvolution.
Figure 11B:
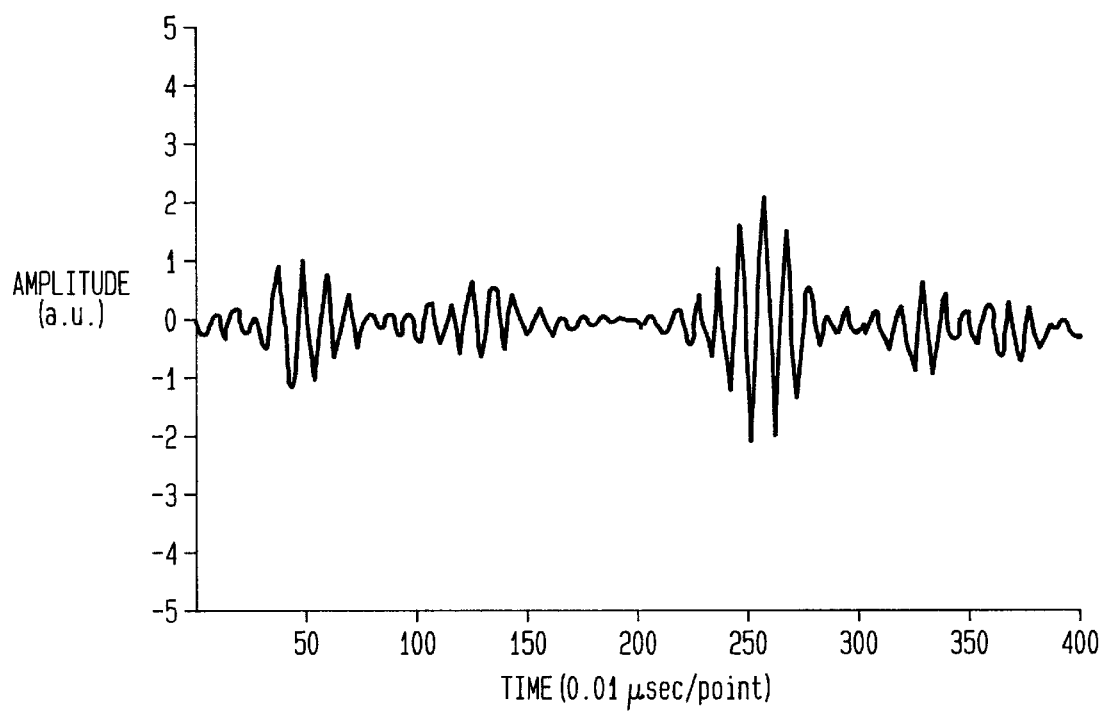
FIG. 11 shows a comparison of predictive deconvolution and dynamic predictive deconvolution.

FIG. 11 compares predictive deconvolution and dynamic predictive deconvolution. The signal in FIG. 11A was obtained from a test specimen which has a crack only at the third thread root. FIG. 11 shows that the dynamic predictive deconvolution is more accurate especially when the reflected signal is obtained from studs (bolts) with cracks.

Figure 12A:
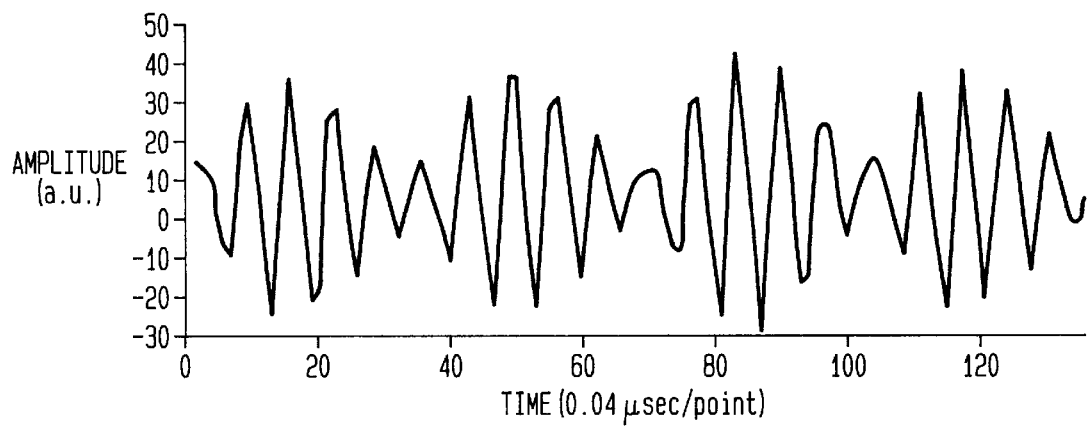
FIG. 12A for signal received at a transducer, FIG. 12B for processed signal by wave shaping, FIG. 12C for processed signal by dynamic predictive deconvolution.
Figure 12B:
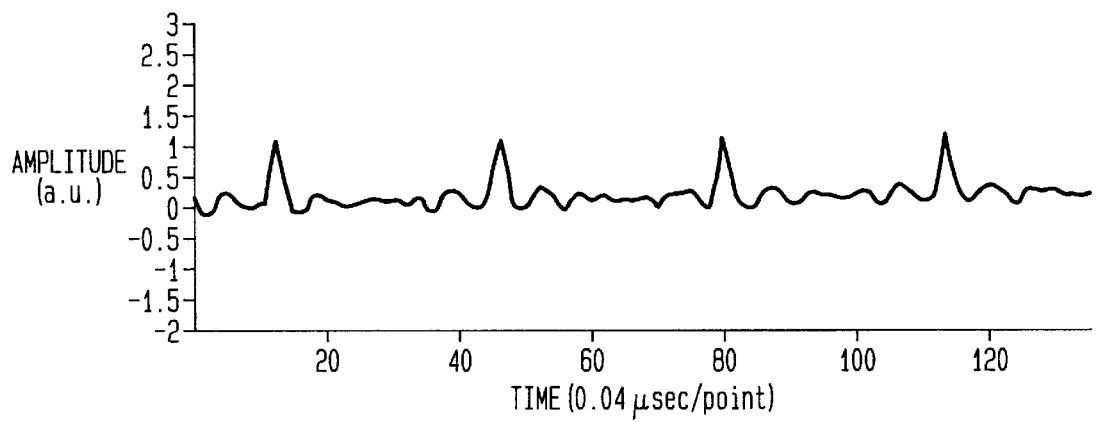
FIG. 12 shows a result of dynamic predictive deconvolution combined with wave shaping.
Figure 12C:
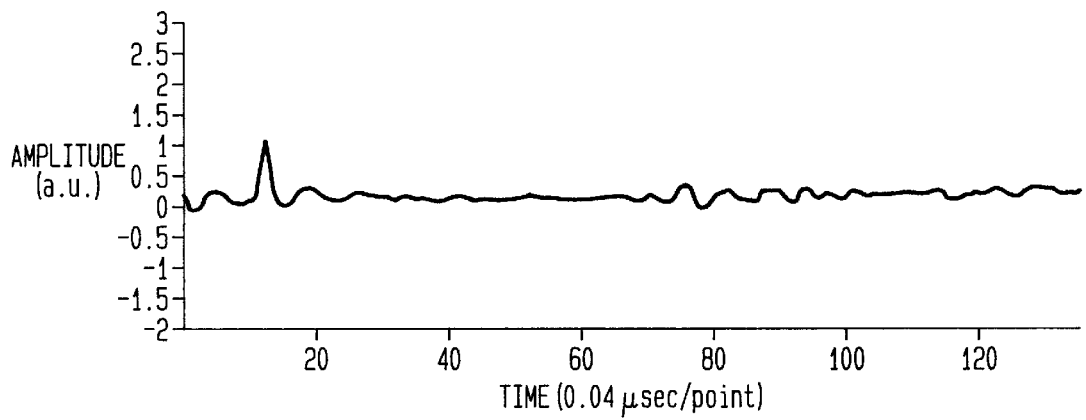

By wave shaping, it is possible to enhance the sharpness of ultrasonic waveforms. Dynamic predictive deconvolution can be applied to the wave shaped signals to give more clear picture of the stud (bolt) status. An example is shown in FIG. 12. From FIG. 12C, it is easy to see that there are no cracks in the thread under inspection.

The above method provides a method which detects and sizes very small cracks in the thread roots of studs and bolts. The key idea is from the observation that the Rayleigh wave propagates slowly along a crack from the tip to the opening and is reflected from the opening mouth. When there exits a crack, a small delayed pulse due to the Rayleigh wave is detected between large regularly spaced pulsed from the thread. The delay time is the same as the propagation delay time of the slow Rayleigh wave and is propagational to the size of the crack. Although there are multiple geometric features in threads of a stud bolt, the Rayleigh wave technique can identify a small crack in the threads as small as 0.5 mm.

To efficiently detect the slow Rayleigh wave, three methods based on digital signal processing has been proposed: modified wave shaping, dynamic predictive deconvolution, and dynamic predictive deconvolution combined with wave shaping. The effectiveness of these methods has been demonstrated by several examples.

In general, there are large number of bolts in a system. Thus, for some applications, it is crucial to decrease the time needed for ultrasonic test. To this end, the fabrication of ASIC(Application Specific Integrated Circuit) for dynamic predictive deconvolution combined with wave shaping is currently under study. Also, it is expected that the proposed methods can be used for ultrasonic inspection of other materials.

What we claim is:

1. A method for detecting and sizing a crack in bolt threads, comprising the steps of:

radiating an ultrasonic wave into the flank of the bolt threads with an incident angle other than 90 degrees;

detecting a reflected signal, which is one of regularly spaced signals which are reflected from the threads;

detecting a Rayleigh wave signal, which is from the Rayleigh wave propagating along the crack from the tip to the opening of the crack and reflected from the crack opening's mouth;

measuring the elapsed time beginning from the reflected signal, and ending at the Rayleigh wave signal; and calculating the crack size by the elapsed time.

2. The method of claim 1 wherein:

the frequency of the radiated ultrasonic wave into the flank of the bolt threads is greater than twice that of the pulse train frequency of the thread signal.

3. The method of claim 1 wherein:

calculating the crack size, h is accomplished by means of the following equation $$h = \Delta t_R V_R V / (V - V_R \sin\theta)$$

where $\Delta t_R$ is the elapsed time beginning from the reflected signal thread and ending at the Rayleigh wave signal, $V_R$ is the Rayleigh wave speed, V is the ultrasonic wave speed, and $\theta$ is the angle between the incident wave and the bolt axis.

4. The method of claim 1 wherein:

the radiated ultrasonic wave into the flank of bolt threads is a longitudinal wave.

5. The method of claim 1 wherein:

the radiated ultrasonic wave into the flank of bolt threads is a shear-wave.

6. The method of claim 1, wherein to enhance the sharpness of the reflected signals, the method further comprises the step of wave shaping by the modified least squares method, which uses a plurality of reference signal from threads without any cracks.

7. The method of claim 1, wherein to compensate for the attenuation of the ultrasonic wave the method further comprises the step of normalizing each signal to unity.

8. The method of claim 1, wherein to efficiently determine the location and the size of a small crack, the method further comprises the step of removing the regularly spaced signals reflected from the roots of the threads.

9. The method of claim 8, wherein in the removing of the regularly spaced signals the method utilizes a dynamic predictive deconvolution where a prediction distance of the regularly spaced signals is adjusted to the location of a transducer which radiates the ultrasonic wave and the structure of the thread.

10. A method for detecting and sizing a crack in bolt threads, comprising:

radiating an ultrasonic wave to the flank of the bolt threads with an incident angle other than 90 degrees;

detecting a tip diffracted signal, which is diffracted from the crack tip;

detecting a reflected signal which is one of regularly spaced signals which are reflected from the threads;

measuring the elapsed time beginning from the tip diffracted signal and ending at the reflected signal; and calculating the crack size by the elapsed time.

11. The method of claim 10 wherein:

the frequency of the radiated ultrasonic wave in the flank of the bolt threads is greater than twice that of the pulse train frequency of the thread signal.

12. The method of claim 10 wherein:

the crack size, h is calculated with the following equation $$h = \Delta t_T V / (2\sin\theta)$$

where $\Delta t_T$ is the elapsed time beginning from the tip diffracted signal and ending at the reflected signal, V is the ultrasonic wave speed, and $\theta$ is the angle between incident wave and the bolt axis.

* * * * *